US00PP15346P2

(12) United States Plant Patent
Koppe

(10) Patent No.: US PP15,346 P2
(45) Date of Patent: Nov. 23, 2004

(54) ***BEGONIA* PLANT NAMED 'BELARO'**

(50) Latin Name: *Begonia×hiemalis*
Varietal Denomination: Belaro

(75) Inventor: Lubbertus H. Koppe, Ermelo (NL)

(73) Assignee: Koppe Royalty B. V., Ermelo (NL)

( * ) Notice: Subject to any disclaimer, the term of this patent is extended or adjusted under 35 U.S.C. 154(b) by 0 days.

(21) Appl. No.: 10/770,207

(22) Filed: Feb. 2, 2004

(51) Int. Cl.[7] ..... A01H 5/00
(52) U.S. Cl. ..... Plt./349
(58) Field of Search ..... Plt./349

*Primary Examiner*—Kent Bell
*Assistant Examiner*—S B McCormick-Ewoldt
(74) *Attorney, Agent, or Firm*—C. A. Whealy

(57) ABSTRACT

A new and distinct cultivar of *Begonia* plant named 'Belaro', characterized by its upright and mounded plant habit; double flowers that are red in color and held above the foliage; and excellent postproduction longevity.

1 Drawing Sheet

Botanical classification/cultivar designation: *Begonia×hiemalis* cultivar Belaro.

BACKGROUND OF THE INVENTION

The present Invention relates to a new and distinct cultivar of *Begonia* plant, botanically known as *Begonia×hiemalis*, commercially known as Elatior *Begonia*, and hereinafter referred to by the name 'Belaro'.

The new *Begonia* was discovered by the Inventor in a controlled environment in Ermelo, The Netherlands, on Feb. 6, 2002, as a naturally-occurring whole plant mutation of *Begonia×hiemalis* cultivar Bela, disclosed in U.S. Plant Pat. No. 13,655. The new *Begonia* was observed as a single plant in a group of flowering plants of the parent cultivar. The selection of this plant was based on its flower coloration.

Asexual reproduction of the new *Begonia* by cuttings taken in a controlled environment in Ermelo, The Netherlands, has shown that the unique features of this new *Begonia* are stable and reproduced true to type in successive generations.

SUMMARY OF THE INVENTION

The cultivar 'Belaro' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Belaro'. These characteristics in combination distinguish 'Belaro' as a new and distinct *Begonia*:

1. Upright and mounded plant habit.
2. Double flowers that are red in color and held above the foliage.
3. Excellent postproduction longevity.

Plants of the new cultivar are most similar to plants of the parent, the cultivar Bela. Plants of the new cultivar differ primarily from plants of the cultivar Bela in flower color as plants of the cultivar Bela have red purple-colored flowers.

BRIEF DESCRIPTION OF THE PHOTOGRAPHS

The accompanying colored photographs illustrate the overall appearance of the new *Begonia*, showing the colors as true as it is reasonably possible to obtain in colored reproductions of this type. Colors in the photographs may differ slightly from the color values cited in the detailed botanical description which accurately describe the colors of the new *Begonia*.

The photograph at the top of the sheet comprises a side perspective view of a typical flowering plant of 'Belaro'.

The photograph at the bottom of the sheet is a close up view of typical developing flowers and leaves of 'Belaro'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Ermelo, The Netherlands, under commercial practice in a glass-covered greenhouse. Average day and night temperature was about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants used for the photographs and the description were about four months old.

Botanical classification: *Begonia×hiemalis* cultivar Belaro.
Commercial classification: Elatior *Begonia*.
Parentage: Naturally-occurring whole plant mutation of *Begonia×hiemalis* cultivar Bela, disclosed in U.S. Plant Pat. No. 13,655.
Propagation:
*Type.*—Cuttings.
*Time to develop roots.*—About 42 days at temperatures of 20° C.
*Root description.*—Fine, fibrous, well-branched and spreading. Plants of the new *Begonia* have not been observed to form tubers.

Plant description:

*Plant form.*—Upright and mounded plant habit, inverted triangle; freely branching with good stem and stem base strength. Flowers are double and abundant. Plants flower continuously.

*Growth habit.*—Moderate growth rate, vigorous. Suitable for 12 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height.*—About 29 cm.

*Plant width.*—About 55 cm.

*Leaves.*—Arrangement: Simple, alternate. Developing leaves, length: About 7 cm. Developing leaves, width: About 5.5 cm. Fully expanded leaves, length: About 13 cm. Fully expanded leaves, width: About 16 cm. Shape: Asymmetrical, more or less reniform. Apex: Acuminate. Base: Cordate. Margin: Doubly serrate. Texture: Mostly glabrous, smooth; slightly pubescent towards the margins. Venation pattern: Palmate. Color: Developing leaves, upper surface: Darker than 147A. Developing leaves, lower surface: Darker than 137A. Fully expanded leaves, upper surface: 191A. Fully expanded leaves, lower surface: Between 191B and 148B. Venation, upper surface: 147B to 147C. Venation, lower surface: 147C. Petiole length: About 6 cm. Petiole texture: Slightly pubescent. Petiole color: 146B overlain with 180A.

Flower description:

*Flowering habit.*—Double flowers with numerous tepals arranged in axillary cymes. Usually 10 to 14 flowers per cyme. Many cymes in flower simultaneously. Flowers positioned above the foliage. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 7 cm. Depth (height): About 1.5 cm.

*Flower buds.*—Length: About 2.3 cm. Diameter: About 1.7 cm. Color: 46A to 46B.

*Tepals.*—Arrangement: Rosette. Quantity per flower: Usually about 25 per flower. Size: Outer tepals: Length: About 3.2 cm. Width: About 5 cm. Inner tepals: Length: About 2.1 cm. Width: About 2.2 cm. Shape: Rounded flabellate. Apex: Rounded. Margin, outer and inner tepals: Slightly crenate. Texture: Smooth, glabrous; satiny. Color: When opening, upper and lower surfaces: Closest to 46B. Fully opened, upper surface: Closest to 46B. Fully opened, lower surface: 47A to 47B.

*Flower bracts.*—Arrangement: Two, opposite. Shape: Broadly cordate. Apex: Apiculate. Margin: Serrate. Texture, upper and lower surfaces: Glabrous, smooth. Color, upper and lower surfaces: 148C overlain with 180A.

*Peduncles.*—Angle: Erect. Length: About 4 cm. Texture: Slightly pubescent. Color: 148A slightly overlain with 175B.

*Pedicels.*—Angle: Erect. Length: About 2 cm. Texture: Pubescent. Color: 148B overlain with 175A.

*Reproductive organs.*—Stamens: None observed. Pistils: None observed.

*Seed/fruit.*—Seed and fruit production have not been observed as reproductive organs are not formed.

Postproduction longevity:

*Individual flowers.*—Generally about two to three weeks.

*Whole plants.*—About six weeks under interior conditions.

Disease/pest resistance: Resistance to pathogens and pests common to *Begonia* has not been observed.

It is claimed:

1. A new and distinct cultivar of *Begonia* plant named 'Belaro', as illustrated and described.

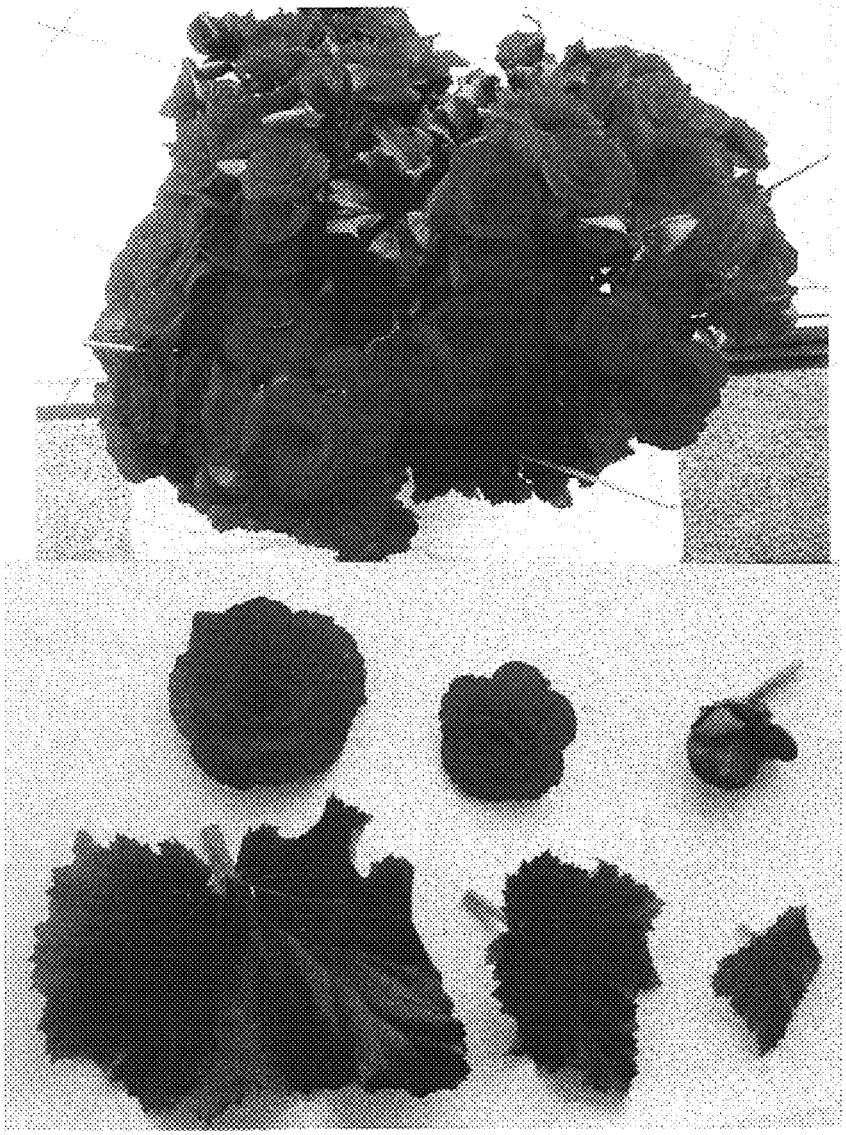

* * * * *